US008695957B2

(12) United States Patent
Quintania et al.

(10) Patent No.: US 8,695,957 B2
(45) Date of Patent: Apr. 15, 2014

(54) COMPACT SUPPORT CLAMP WITH ROTATING EQUIPMENT ATTACHMENT AND JAW OPERATOR

(75) Inventors: Richard Enoch Quintania, Fallbrook, CA (US); James Mark Cox, Winchester, CA (US)

(73) Assignee: Pryor Products, Oceanside, CA (US)

( * ) Notice: Subject to any disclaimer, the term of this patent is extended or adjusted under 35 U.S.C. 154(b) by 508 days.

(21) Appl. No.: 12/610,216

(22) Filed: Oct. 30, 2009

(65) Prior Publication Data

US 2011/0101587 A1    May 5, 2011

(51) Int. Cl.
*B25B 1/22*    (2006.01)
*A47F 5/00*    (2006.01)

(52) U.S. Cl.
USPC .......................................... 269/74; 248/309.1

(58) Field of Classification Search
USPC ........... 269/249, 143, 43, 271, 32; 248/219.1, 248/176.1, 218.4, 229.15, 229.25, 230.6, 248/229.14, 229.12, 229.24, 229.22, 230.3, 248/230.5, 231.61
See application file for complete search history.

(56) References Cited

U.S. PATENT DOCUMENTS

| 1,106,096 | A | 8/1914 | Hunt |
| 2,316,073 | A | 4/1943 | Kellogg |
| 3,570,836 | A | 3/1971 | Pettavel |
| 4,693,656 | A | 9/1987 | Guthrie |
| 6,896,232 | B2 | 5/2005 | Crowell |
| 2006/0231714 | A1 * | 10/2006 | Crain et al. ................ 248/309.1 |

* cited by examiner

*Primary Examiner* — Lee D Wilson
*Assistant Examiner* — Nirvana Deonauth
(74) *Attorney, Agent, or Firm* — Gordon & Rees LLP

(57) ABSTRACT

The device utilizes a thruster cylinder driven by a enlarged knob and terminating in a thruster plate to clamp to a support. Provision is made to attach a device to the clamp through a rotating index wheel which can lock the device by receiving a tang from a trigger lever at a selected increment of rotation. A second embodiment has two index wheels so that the attached device can be displaced in one of four directions to avoid conflict with other devices on the same support. The second axis is normally used to return a displaced device to an upright orientation.

28 Claims, 7 Drawing Sheets

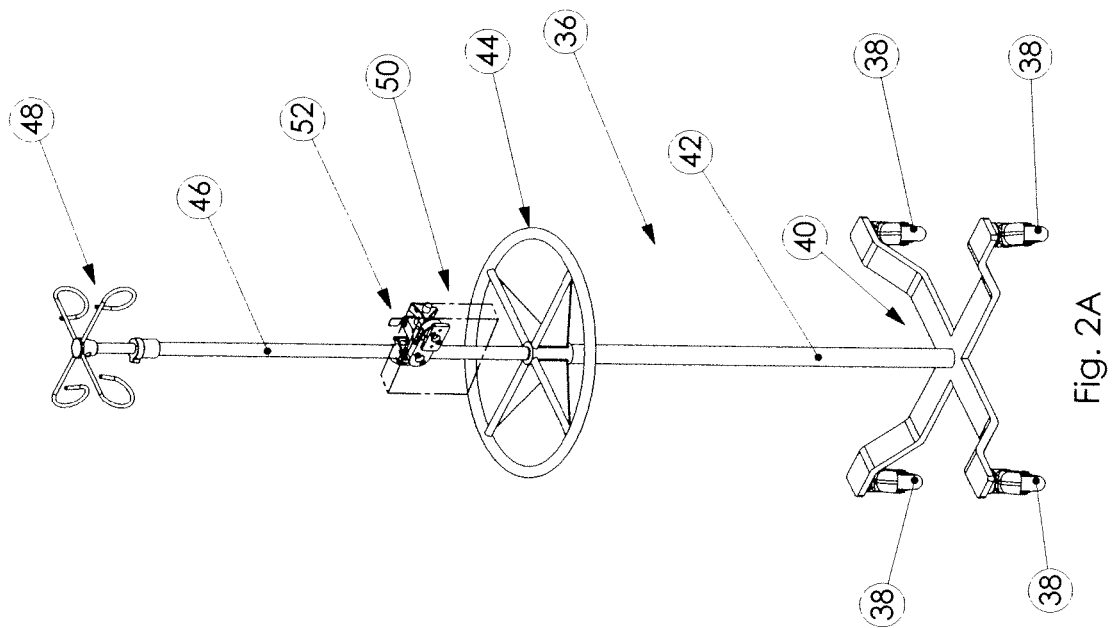
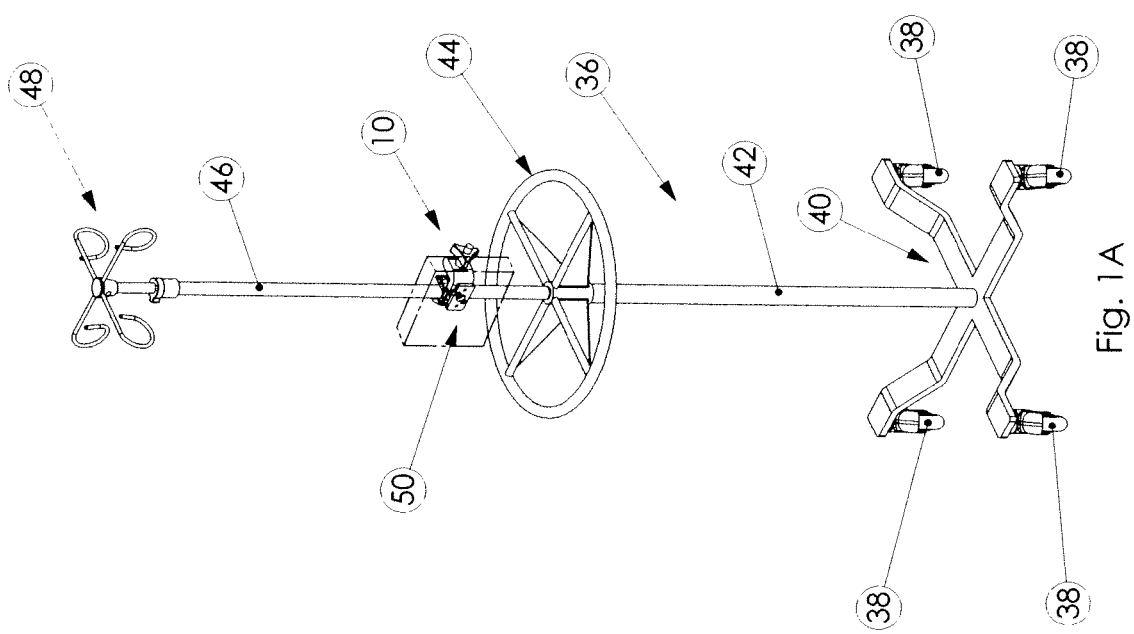

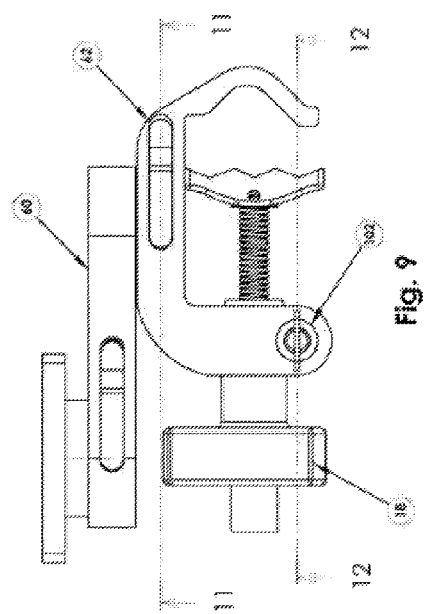
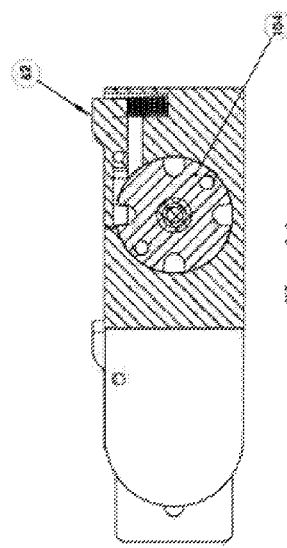
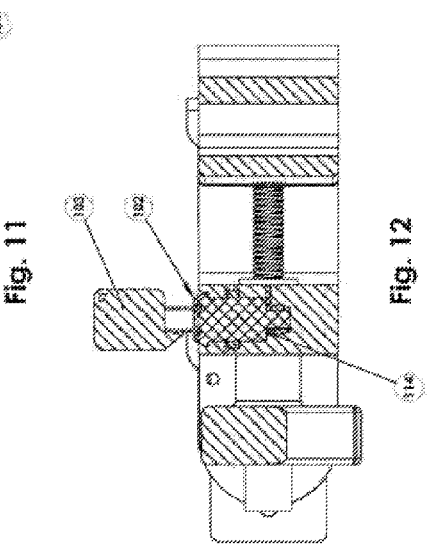

COMPACT SUPPORT CLAMP WITH ROTATING EQUIPMENT ATTACHMENT AND JAW OPERATOR

BACKGROUND OF THE INVENTION

In various applications structures such as equipment must be mounted from a support in proximity to the location where the equipment is utilized. This requirement is especially common with medical equipment that must be supported near where the equipment is utilized for medical treatment of patients.

Clamps with features for mounting equipment are known that are secured to existing supports such as tubular supports as in IV poles (vertical) and bed rails (horizontal). Clamps have also been utilized with planar supports such as table edges.

A typical clamp may comprise a c-clamp shape that grasps a support between a fixed jaw and a moveable jaw. The jaw operator mechanism for moving the moveable jaw into engagement with and securely grasping the support has typically utilized a screw carried in a threaded opening in the clamp body. This screw, of necessity, must be of a length greater than the maximum distance between the fixed and moveable jaws plus the width of the clamp body through which it is threaded. This creates an elongated profile that may interfere with other clamps or structures carried on the support.

Another feature which is desirable in equipment clamps is the ability to rotate attached equipment so that the equipment will be presented to the user in a upright orientation. In the past rotational capability has required substantial further protrusions from the clamp body to accommodate the rotational mechanism which further increases the profile of the clamp and the potential for interference with other clamps or structures on the support.

Various suggestions have been made that changes should be made to clamp designs including the suggestion of incorporating a lock to prevent removal of the clamp from the support on which the clamp is mounted and thereby to prevent removal of the device by unauthorized persons. It has also been suggested that it would be advantageous to reduce the overall width of the clamp by reducing the height of the structures used for rotation of the supported device. However, no structure to accomplish these objectives has been suggested.

The present invention represents a realization of the deficiencies of prior art clamps and the development of mechanisms that minimize the profile and versatility of equipment support clamps.

SUMMARY OF THE INVENTION

Locks on clamps for medical devices are part of the prior art, as are small diameter knobs, that can be used to advance or retract a threaded device rapidly when there is little or no resistance to the screws advance or retraction. These features of the exemplary embodiment are claimed as part of the invention only when combined with the unique combination of features in the disclosed embodiment.

In an exemplary embodiment all advantages know to the applicant at the time of filing are incorporated. In the invention a compact clamp and mount is provided for attaching equipment such as medical devices to a support. The clamp incorporates a moveable thruster plate which cooperates with a fixed jaw. The clamp is capable of mounting equipment from horizontal supports (such as a table edge or bed rail) and from vertical supports (such as an IV pole). Both cylindrical and flat supports are accommodated by shape of the thruster plate and fixed jaw. After installation the equipment can be rotated on the clamp so that the equipment is in an upright orientation. In a modified embodiment dual rotational adjustment is accommodated for allowing an adjustment to device such as in the vertical plane, so that the equipment can be position in a way that both makes it easy for the user to observe, for example, controls and displays on the equipment and at the same time avoid interference with other equipment or structures that may be carried on the same support.

The clamp body incorporates all necessary functions in much less space than conventional clamps. The functions that may be accommodated include indexed rotation, clamp jaw or thruster plate advance and retraction without threaded extensions outside of the clamp body, and a lock to prevent unauthorized removal of the equipment from the support, and an indexed rotation wheel.

Indexed rotation is accomplished within the clamp body by incorporating a wheel recess with a central spindle about which the index wheel can rotate. The rotation of the wheel is controlled by a spring return trigger that retracts a tang from spaced index recesses in the periphery of the wheel to permit rotation to a selected indexed position. A nominal 90 degree spacing is shown. A mount plate is secured for rotation with the index wheel and incorporates an access opening to provide access to a bolt that is threaded into the central shaft. The equipment is carried on the mount plate.

The advance and retraction of the clamp jaw is accomplished through a thruster cylinder that surrounds a threaded bolt attached to the thruster. A enlarged knob is attached to the cylinder which is threaded to engage the bolt near the outer end of the cylinder. The enlarged knob is sized to be easily grasped by the fingers and yet provide sufficient leverage to firm drive the thruster plate into engagement with a support. A left handed thread is provided so that clockwise rotation of the enlarged knob results in extension of the thruster plate to engage the support, which is what the user would intuitively expect from clockwise rotation.

The clamp body may optionally incorporate a lock to prevent substantial rotation of the enlarged knob and therefore prevent removal of the equipment from the support. A tubular cam lock is received in a cylindrical recess in the outer perimeter of the clamp body. A lock lever is mounted at the inner end of the lock body. When a key is rotated to the locked position the lock lever rotates to where it is adjacent to the thruster cylinder. The cylinder mounts a nub that extends from the cylinder so that the path of the nub intersects the position of the lock lever when the enlarged knob is rotated to the locked position and limits rotation of the cylinder to less than 360 degrees. This amount of rotation is not enough to disengage the clamp from cylindrical or square tubing supports.

In a further embodiment of the invention, two rotational elements are incorporated so that the position of the attached equipment can be varied to limit interference between multiple clamps attached to the same support. The second index plate is mounted in a recess in an arm which is in turn carried on the first index plate. The arm comprises an elongated plate and has sufficient thickness to incorporate the recess for the index plate which limits the offset of the associated mount plate from the clamp body.

BRIEF DESCRIPTION OF THE DRAWINGS

FIG. 1A shows the clamp of FIG. 1, mounted on a wheeled IV stand and carrying a piece of equipment shown in dotted lines.

FIG. 2A shows a two axis clamp mounting a piece of equipment (shown in dotted lines) on a wheeled IV stand.

FIG. 9 is a top plan view of the clamp in FIG. 8.

FIG. 11 is a sectional view taken on line 11-11 in FIG. 9 and showing the second index wheel and trigger assembly.

FIG. 12 is a sectional view taken on line 12-12 in FIG. 9 and showing the lock cylinder and lock lever.

DETAILED DESCRIPTION OF THE DRAWINGS

Figure 1:
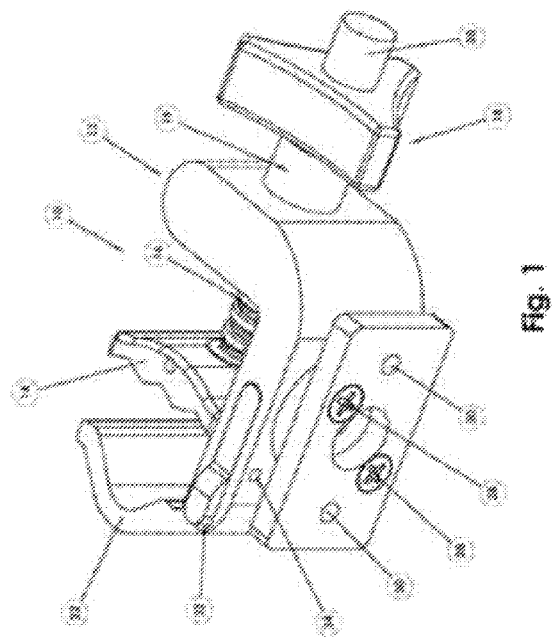
FIG. 1 is a perspective view of the clamp and mount of the invention with provisions for rotation about one axis.

FIG. 1 shows the single rotational axis clamp (10) with a clamp body (12). The thruster plate (14) is attached to a screw (16) that is advanced/retracted by operation of the enlarged knob (18) which rotates the thruster cylinder (See FIG. 4). The thruster cylinder is in threaded engagement with the screw (16). The enlarged knob (18) has a knurled extension (20) for rapid rotation to bring the thruster plate (14) into engagement with a support (not shown) and to retract the thruster plate (14) after the tension on the support is released by use of the enlarged knob (18). The enlarged knob has a cylindrical extension (19) which surrounds the thruster cylinder and thereby provides room for the screw (16) to retract. The clamp (10) has a fixed jaw (22) opposed to the thruster plate (14). A mount plate (24) is secured to a index wheel (26) (See FIG. 4) by fasteners (28). The mount plate incorporates two mounting bores (30) through which fasteners can be passed to secure to a piece of equipment or other structure to the clamp (10). A trigger (32) is shown received in the clamp body (12) and carried on a pivot (34). The operation of the trigger (32) and index wheel (26) will be explained in greater detail by reference to FIG. 6.

Aluminum is the preferred material for the clamp body and most of the associated parts to produce a light-weight yet strong device that does not substantially increase the total weight of the clamp and any associated medical equipment. However it has been found desirable to make the thruster plate of molded nylon 66 fiber reinforced plastic to avoid marring the surfaces of a support carrying the clamp and yet retain the strength and toughness to withstand substantial clamping pressure. It was also determined that the index wheel should be made of a material complementary to the characteristics of the aluminum body and particularly the index wheel. Therefore brass is the preferred material for the index wheel and will smoothly engage and disengage with the trigger tang over a long operational life.

FIG. 1A shows the clamp (10) mounted on a wheeled IV stand (36). The stand has wheels (38) on a base (40) with a vertical support (42) mounting a support wheel (44) (for use by ambulatory patients). The vertical support (42) carries a vertical IV pole (46) topped by an adjustable IV tree (48). A piece of equipment (50) is shown in dotted lines. The equipment may be an IV pump, heart monitor or other instrument or structure requiring support.

Figure 2:
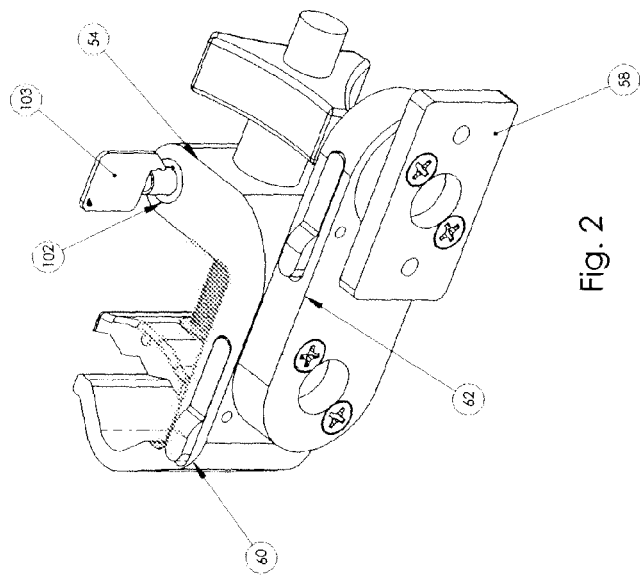
FIG. 2 is a perspective view of the clamp and mount of the invention with provision for rotation about two axes and a cylindrical lock.
Figure 7:
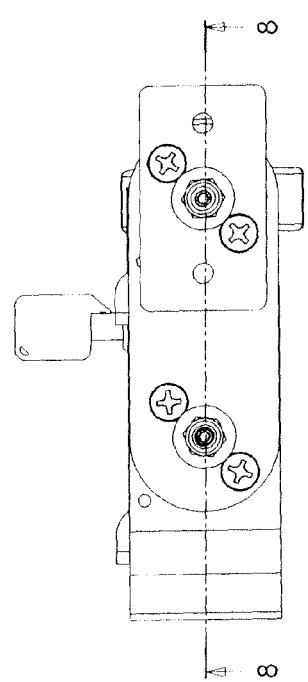
FIG. 7 is a side view of the dual axis clamp of FIG. 2.

FIG. 2 shows a two axis clamp (52) having a clamp body (54). An elongated arm (56) provides an offset for the mount plate (58) which is in turn carried on an index wheel mounted in a recess (60) (See FIG. 8) in the elongated arm (56). Two triggers are provided to control rotation. Trigger (60) controls rotation of the arm (56) on the clamp body (54) and trigger (62) controls rotation of the mount plate (58) on the arm (56). By use of the trigger (60) a mounted structure such as a piece of medical equipment mounted on a vertical support (as in FIG. 2A) can be displaced horizontally by double the distance between the axes of the two index plates (See FIG. 8) by depressing the trigger (60) and rotating the arm (56) by 180 degrees. By comparing the position of the equipment (50) in FIG. 1A (single axis) to that in FIG. 2A (two axis with the elongated arm horizontal) it will be appreciated that the two axis embodiment can be used to vary the location of the equipment relative to the support (IV pole (36) in the illustrated examples).

Referring again to FIG. 2, the second trigger (62) controls the rotational orientation of the equipment. For example, if the arm (56) is rotated 90 degrees to the left to a vertical orientation it will displace the attached equipment upwardly. The second trigger (62) is then operated to permit rotation of the displaced equipment to the left to return it to an upright orientation. It will be apparent that the two axis configuration can be used in a similar manner when the clamp is carried on a horizontal support with the first rotation of the taking the arm to the horizontal to one side or the other and the rotation of the mount plate again being used to return the equipment to an upright orientation.

Figure 3:
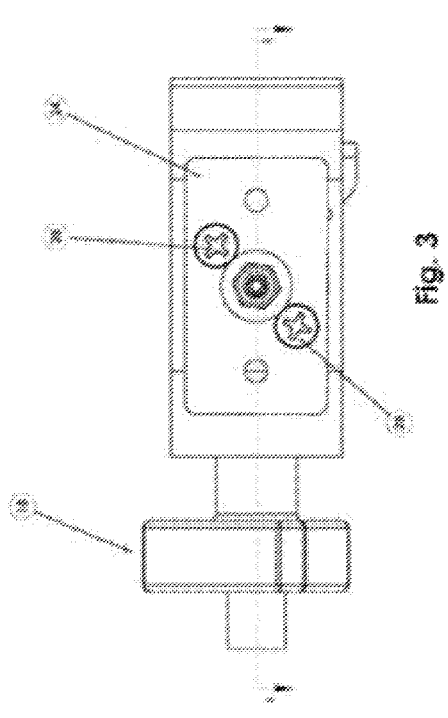
FIG. 3 is a side view of FIG. 1 showing the provisions for attachment of the mount plate and access to the fastener that secures the rotational elements in a recess in the clamp body.
Figure 4:
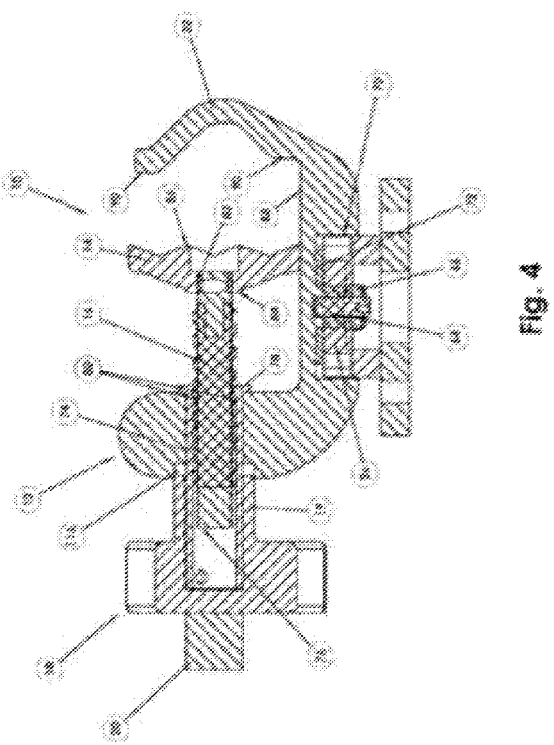
FIG. 4 is a sectional view taken along line 4-4 of FIG. 3 and showing the cylindrical thruster and recessed index wheel.

FIGS. 3 and 4 show the mount plate (24) in a single axis embodiment. The mount plate is attached to a threaded spindle (64) (See FIG. 4) by a fastener such as the nylon insert nut (66). Screws (28) are threaded into the index wheel through threaded bores (68) (See FIG. 6). Accordingly the mount plate (24) rotates on the spindle (64) as determined by the indexed orientation of the index wheel (70). The arrangement of the spindle being located in a recess (72) within the clamp body (12) permits a minimal addition to the width of the clamp body to accommodate the rotation.

FIG. 4 shows the index wheel (70) journaled on the spindle (64) which is received in a cylinder (66) within the recess (72) that houses the index wheel (70). The spindle (64) is at right angles to the axis of the thruster cylinder. The enlarged knob (18) through the cylindrical extension (19) is shown as being secured to the thruster cylinder (74) by a pin (76). The pin (76) cooperates with the shoulder (78) on the thruster cylinder and the cylindrical extension (19) to capture the enlarged knob (18) and thruster cylinder (74) in the clamp body (12). Rotation of the enlarged knob (18) results in rotation of the thruster cylinder (74). The thruster cylinder is shown to have threads (80) at its terminal end which engage the screw (16). Thus the enlarged knob and cylinder rotate together and form a rotatable drive structure.

Rotation of the thruster cylinder (74) results in extension/retraction of the screw (16). The screw (16) does not rotate. It is through the use of the cylinder and screw combination that maximum length profile of the clamp (10) is reduced. The screw extends and retracts from within the cylinder and enlarged knob (18) so the enlarged knob (18) and does not move away from the clamp body (12) as in conventional designs increase the effective length as the jaw is retracted. The screw (16) is preferably configured with a left-hand thread. By using a left hand thread, clockwise rotation of the enlarged knob (18) results in the advance of the clamp jaw as a user would intuitively expect and avoids the confusion that would result if a right hand thread were employed.

Because the screw does not rotate the terminus (82) of the screw can be locked onto the jaw (14). The thruster plate (14) will preferably be in the form of a waffle plate (86) with ridges (84) that allow the jaw to securely engage a variety of surfaces on a support such as the IV pole in FIGS. 1A and 2A or to horizontal bars or planar horizontal surfaces. The waffle plate (86) is guided by engagement with the face (88) of the clamp body. The face (88) is flat so there is no tendency for the waffle plate to twist when it is extended toward the fixed jaw (22). The flats (90) on the fixed jaw (22) are useful for providing a substantial flat area for engaging planar surfaces.

Figure 5:
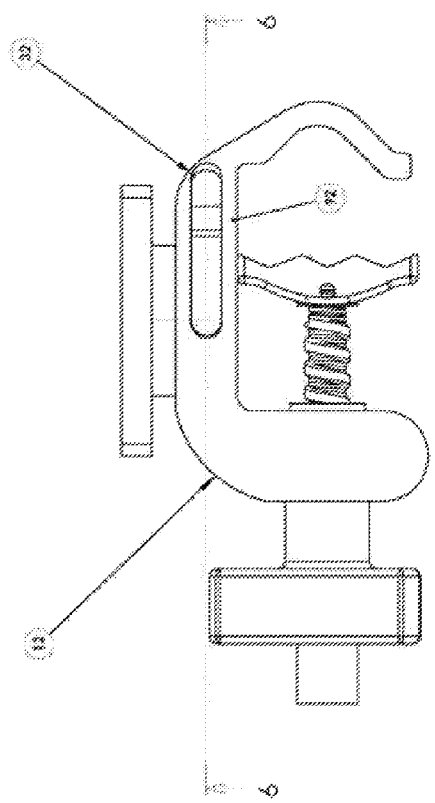
FIG. 5 is a top plan view of the clamp of FIG. 1.

FIG. 5 shows the location of the trigger (32) within the closed side (92) of the clamp body (12).

Figure 6:
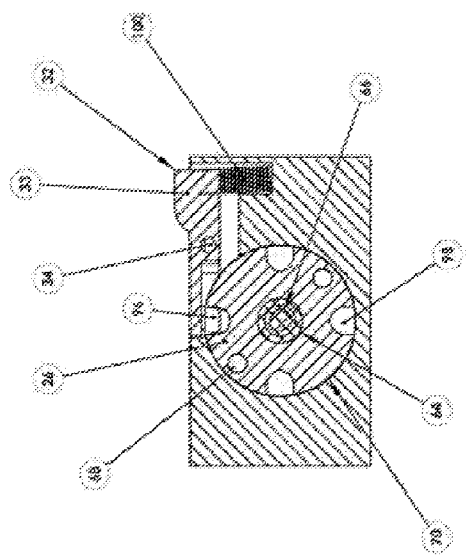
FIG. 6 is a sectional view taken along line 6-6 of FIG. 5 and showing the trigger with associated tang engaging index openings of the index wheel.

FIG. 6 shows the trigger assembly (32) which includes the trigger lever (33) journaled on a pivot (34) and terminating in a tang (96) which is sized to fit into an index recess such as the exemplary recess (98) on the index wheel (70). The trigger tang (96) is held in engagement with an index recess (98) on the index wheel (70) by spring (100) so that the clamp will remain in a selected rotational orientation until the trigger (32) is depressed to withdraw the tang (96) free of the index recess (98). The index wheel (70) is shown to have threaded bores (68) which correspond to the openings in the mount plate (see FIG. 3).

FIG. 7-13 shows the two axis embodiment of the invention and also illustrates the use of a cylinder lock (102) (See FIG. 12) by utilization of the key (103) to prevent the removal of the clamp body (52) and thereby prevent the removal of the associated equipment.

Figure 8:
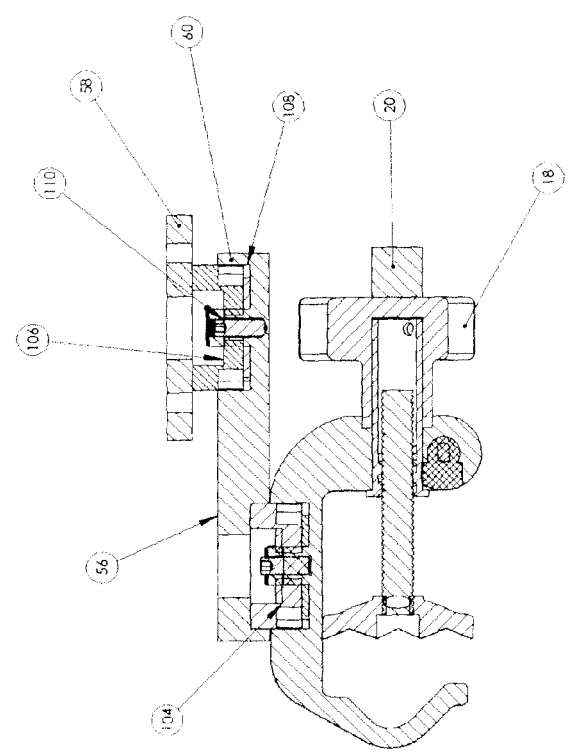
FIG. 8 is a sectional view taken along line 8-8 of FIG. 7 showing the lock cylinder being received in the clamp body outboard of the cylindrical thruster.

FIG. 8 shows the first index wheel (104) mounts an elongated arm (56) instead of mounting the equipment directly as in the single axis version. The elongated arm (56) houses a second index wheel (106) with structure that duplicates the first index wheel except that the recess (108) which houses the second index wheel (106) is within the arm (56) instead of the clamp body (52). The recess (108) is at the end opposite to that attached to the clamp body. The use of a spindle (110) allows most of the structure for rotation to be housed within the body of the arm (56), rather than extending extensively beyond the surface of the arm. The result is a much lower width profile than can be achieved by conventional means. The mourning plate (58) in the two axis embodiment is offset from the axis of the index wheel (104) mounted in the clamp body (54) so that the mounted equipment may be positioned vertically above, below or the sides of that axis and thereby position to the equipment so that it does not interfere with other mourned equipment or structure on the support. As will appear the lock cylinder (102) is housed within the clamp body (54) and doesn't further enlarge the profile of the clamp when no key (103) is inserted.

FIG. 9 is full line rendering of the device as in FIG. 8 showing the enlarged knob (18), the triggers (60) and (62).

Figure 9A:
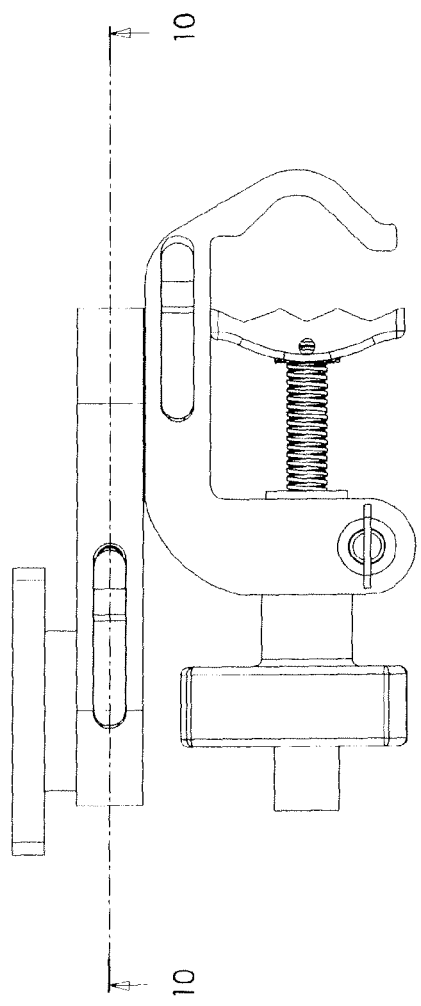
FIG. 9A is a view identical to FIG. 9, except for the position of the section line utilized by FIG. 10.
Figure 10:
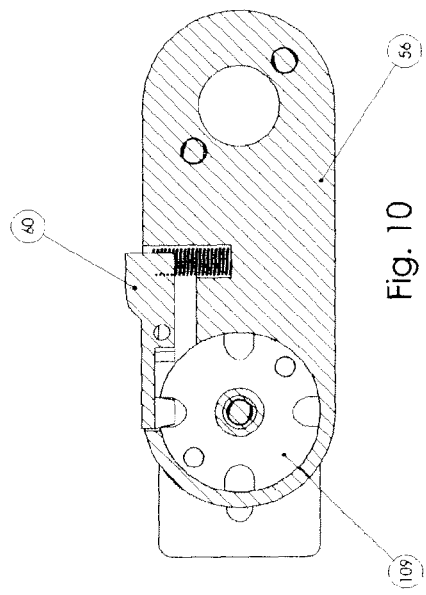
FIG. 10 is a sectional view taken along line 10-10 of FIG. 9A and showing the elongated arm with index wheel at one end and provisions for mounting a mount plate at the other end.

FIG. 9A is the same as FIG. 9 except that the section line 10-10 is placed so that the section view in FIG. 10 is positioned to show the index wheel (109) as is illustrated in FIG. 10.

FIG. 10 is a sectional view taken on line 10-10 of FIG. 9A and showing the index wheel (109) and trigger (60) as received for rotation within the elongated arm (56).

FIG. 11 shows index wheel (104) and the trigger (62).

Figure 13A:
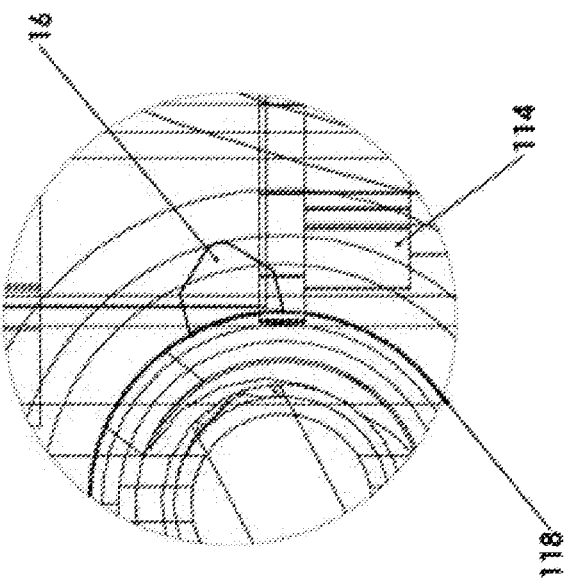
FIG. 13A is a detail view of the engagement between the nub on the thruster cylinder, and showing the lock lever in position to engage the nub on the thruster cylinder.

FIG. 12 shows the detail of a cylinder lock and key. The cylinder lock (102) has a lock lever (114) which is used to engage a nub (116) on the cylindrical extension (19) (see FIGS. 4 and 13A).

Figure 13:
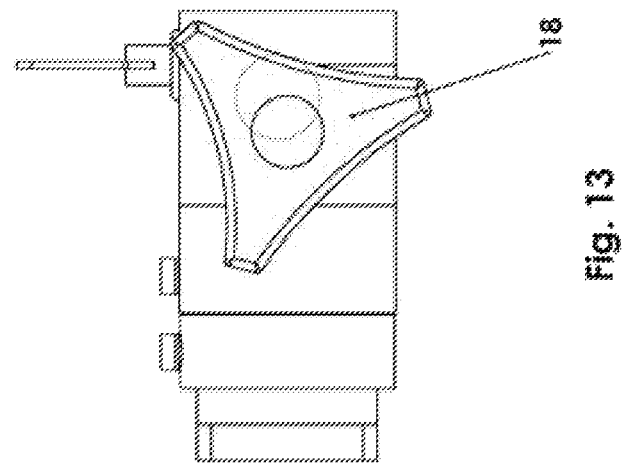
FIG. 13 is an end view of the clamp (52) to show the position of the detail view of the lock cylinder viewed from below.

FIG. 13 shows the location 13 of the detail view in FIG. 13 (detail). The detail is an enlarged view of the cylinder lock as seen from below FIG. 13. The nub (116) is attached to the cylindrical extension (19). The nub (116) engages the lock lever (114) as the Enlarged knob (18), cylindrical extension (19) and thruster cylinder (118) (collectively the rotatable drive structure) are rotated through less than 360 degrees. Since the rotatable drive structure can not be rotated even a full turn it is not possible to remove the clamp from a cylindrical support because the thruster plate (118) (See FIGS. 2 and 8) cannot be made to clear the cylindrical support.

Having described our invention, we now claim:

1. A compact clamp for mounting and positioning a structure on a support, comprising:
   a clamp body having a generally C-shaped profile with a fixed jaw and thruster plate adapted to capture a support between said jaw and plate,
   a thruster cylinder rotateably received through said clamp body and having threads on the cylinder that surrounds a screw received in said cylinder, and
   said screw threadably engaging said cylinder so that when the cylinder is rotated the screw is advanced or retracted to move said thruster plate into and out of engagement with said support,
   a first mount plate structurally connected to said clamp body through at least one index wheel,
   a recess in said clamp body for receiving said index wheel,
   said index wheel having a plurality of index recesses into which a rotation tang can be received to lock said mount plate in a selected rotational orientation.

2. The compact clamp according to claim 1, further comprising:
   a second mount plate and second index wheel connected to said first mount plate and index wheel by an elongated arm,
   said elongated arm having a recess receiving said second index wheel.

3. The compact clamp according to claim 2, further comprising:
   a trigger lever mounted on a pivot carried in said clamp body and carrying said tang on said trigger lever spaced from said pivot for engagement with said index openings on said index wheel.

4. The compact clamp according to claim 3, further comprising:
   a trigger spring in said clamp body and pressing said tang into engagement with said index openings on said index wheel.

5. The compact clamp according to claim 2, further comprising:
   said index wheel has index openings are at least two 90 degree intervals.

6. The compact clamp according to claim 2, further comprising:
   said thruster plate having a central curved section for engagement with generally cylindrical supports and at least one flat terminal section for engagement with planar supports.
7. The compact clamp according to claim 2, further comprising:
   a knob for rotating a rotatable drive structure said rotatable drive structure having at least one nub that protrudes from said thruster cylinder,
   a lock received in said clamp body and having a lock lever mounted for rotation into and out of interference with the rotational path of said nub.
8. The compact clamp according to claim 7, further comprising:
   said lock is received in said clamp body adjacent to said thruster cylinder and outboard in said clamp body from the location where said rotatable drive structure is rotateably received in said clamp body.
9. The compact clamp according to claim 2, further comprising:
   a trigger lever mounted on a pivot carried in said elongated arm and carrying a tang on said trigger lever spaced from said pivot for engagement with index openings on said second index wheel.
10. The compact clamp according to claim 2, further comprising:
    an enlarged knob attached to said thruster cylinder to facilitate rotation of said thruster cylinder by hand.
11. The compact clamp according to claim 10, further comprising:
    a knurled extension on said enlarged knob and having a smaller diameter than said enlarged knob to facilitate rapid rotation of said enlarged knob when there is low resistance to rotation.
12. The compact clamp according to claim 1, further comprising:
    a trigger lever mounted on a pivot carried in said clamp body and carrying said tang on said trigger lever spaced from said pivot for engagement with said index openings on said index wheel.
13. The compact clamp according to claim 12, further comprising:
    a trigger spring in said clamp body and said spring pressing said tang into engagement with said index openings on said index wheel.
14. The compact clamp according to claim 12, further comprising:
    said index wheel has index openings are at least two 90 degree intervals.
15. The compact clamp according to claim 12, further comprising:
    said thruster plate having a central curved section for engagement with generally cylindrical supports and at least one flat terminal section for engagement with planar supports.
16. The compact clamp according to claim 12, further comprising:
    said rotatable drive structure having at least one nub that protrudes from said rotatable drive structure,
    a cylindrical lock received in said clamp body and having a lock lever mounted for rotation into and out of interference with the rotational path of said nub.
17. The compact clamp according to claim 16, further comprising:
    said cylindrical lock is received in said clamp body adjacent to said rotatable drive structure and outboard in said clamp body from the location where the rotatable drive structure is rotateably received in said clamp body.
18. The compact clamp according to claim 12, further comprising:
    an enlarged knob attached to said thruster cylinder to facilitate rotation of said thruster cylinder by hand.
19. The compact clamp according to claim 18, further comprising:
    a knurled extension on said enlarged knob and having a smaller diameter than said enlarged knob to facilitate rapid rotation of said enlarged knob when there is low resistance to rotation.
20. A compact clamp for mounting and positioning a structure on a support, comprising:
    a clamp body having a generally C-shaped profile with a clamp jaw and thruster plate adapted to capture a support between said jaw and plate,
    a thruster cylinder rotateably received through said clamp body
    a screw received in said cylinder and threadably engaging said cylinder so that when the cylinder is rotated the screw is advanced or retracted to move said thruster plate into and out of engagement with said support,
    a first mount plate structurally connected to said clamp body and adapted to be secured to a structure to be supported.
21. A compact clamp for mounting and positioning a structure on a support, comprising: a clamp body having a generally C-shaped profile with a clamp jaw and thruster plate adapted to capture a support between said jaw and thruster plate, a screw engaging said thruster plate to extend and retract said thruster plate a first mount plate structurally connected to said clamp body through at least one index wheel, a recess in said clamp body for receiving said index wheel, said index wheel rotating at right angles to said screw, said index wheel having a plurality of index openings into which a rotation tang can be received to lock said mount plate in a selected rotational orientation, said elongated arm having a recess receiving said second index wheel, a second mount plate and second index wheel connected to said first mount plate and a first index wheel of the at least one index wheel by an elongated arm, said elongated arm having a recess receiving said second index wheel.
22. The compact clamp according to claim 21, further comprising:
    a trigger lever mounted on a pivot carried in said clamp body and carrying said tang on said trigger lever spaced from said pivot for engagement with said index openings on said first and second index wheels.
23. The compact clamp according to claim 22, further comprising:
    a trigger spring in said clamp body and pressing said tang into engagement with said index openings on said first and second index wheels.
24. The compact clamp according to claim 20, further comprising: said thruster plate having a central curved section for engagement with generally cylindrical supports and at least one flat terminal section for engagement with planar supports.
25. A compact clamp for mounting and positioning a structure on a support, comprising:
    a clamp body having a generally C-shaped profile with a fixed jaw and a thruster plate adapted to capture a support between said jaw and plate, a thruster cylinder rotateably received through said clamp body and having threads on the cylinder that surrounds a screw received in said cylinder, and said screw threadably engaging said cylinder so that when the cylinder is rotated the screw is advanced or retracted to move said thruster plate into and out of engagement with said support, a first mount plate structurally connected to said clamp.

26. The compact clamp according to claim 25, further comprising:

said thruster plate having a central curved section for engagement with generally cylindrical supports and at least one flat terminal section for engagement with planar supports.

27. The compact clamp according to claim 26, further comprising: an enlarged knob attached to said thruster cylinder to facilitate rotation of said thruster cylinder by hand.

28. The compact clamp according to claim 27, further comprising:

a knurled extension on said enlarged knob and having a smaller diameter than said enlarged knob to facilitate rapid rotation of said enlarged knob when there is low resistance to rotation.

* * * * *